(12) United States Patent
Osborne et al.

(10) Patent No.: US 6,544,269 B2
(45) Date of Patent: Apr. 8, 2003

(54) LOCALIZER NEEDLE

(75) Inventors: Thomas A. Osborne, Bloomington, IN (US); Kurt J. Tekulve, Ellettsville, IN (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/897,246

(22) Filed: Jul. 2, 2001

(65) Prior Publication Data

US 2002/0019595 A1 Feb. 14, 2002

Related U.S. Application Data

(60) Provisional application No. 60/224,228, filed on Aug. 10, 2000.

(51) Int. Cl.[7] .............................................. A61B 17/34
(52) U.S. Cl. ....................................................... 606/116
(58) Field of Search ........................ 600/562, 564–567; 606/116, 185; 140/67, 102, 111, 149

(56) References Cited

U.S. PATENT DOCUMENTS

| | | | |
|---|---|---|---|
| 4,799,495 A | 1/1989 | Hawkins et al. | 128/754 |
| 4,986,279 A | 1/1991 | O'Neill | 128/754 |
| 5,059,197 A | 10/1991 | Urie et al. | 606/116 |
| 5,127,916 A | 7/1992 | Spencer et al. | 606/185 |
| 5,197,482 A | 3/1993 | Rank et al. | 128/749 |
| 5,234,426 A | 8/1993 | Rank et al. | 606/1 |
| 5,749,887 A | 5/1998 | Heske et al. | 606/185 |
| 5,954,655 A | 9/1999 | Hussman | 600/478 |
| 6,053,925 A | 4/2000 | Barnhart | 606/116 |

OTHER PUBLICATIONS

A Modified Needle–Hookwire Technique to Simplify Preoperative Localization of Occult Breast Lesions; D. Kopans, & S. DeLuca; Technical Notes; vol. 134; pp. 781.

Versatile Spring Hookwire Breast Lesion Localizer; D. Kopans & J. Meyer; AJR; vol. 138, Mar. 1982; pp. 586–587.

Spring Hookwire Breast Lesion Localizer: Use with Rigid –compression Mammographic Systems; D. Kopans, L. Lindfors, K. McCarthy, & J. Meyers; Radiology; vol. 157, No. 2; Nov. 1985; pp. 537–538.

Prototype Breast Coil for MR–Guided Needle Localization; S. Heywang–Köbrunner, A. Huynh, P. Viehweg, W. Hanke, H. Requardt, & I. Paprosch; Journal of Computer Assisted Tomography; A Radiological Journal Dedicated to the Basic and Clinical Aspects of Reconstructive Tomography; vol. 18, No. 6, Nov./Dec. 1994; pp. 876–881.

Disposable Kopans Breast Lesion Localization Needles; Breast Lesion Localizer; Cook Product Catalogue.

*Primary Examiner*—Max F. Hindenburg
(74) *Attorney, Agent, or Firm*—Brinks Hofer Gilson & Lione

(57) ABSTRACT

A medical device (10) includes at least a stylet (12) for establishing the location of tissue of interest, such as a nonpalpable lesion in breast tissue. The device may also include a needle assembly (14) and an aspiration syringe (16). The medical device (10) can most readily be understood as an improvement in Kopans-type or hookwire-type localizer stylet having a wire shaft (18) with a distal end (28), and a hook (36) depending in a proximal direction from the wire shaft (18). The improvements entail spacing the hook (36) proximally of the distal end (28) of the wire shaft (18), and providing the wire shaft with a twist between the hook (36) and the distal end (28) of the wire shaft (18). Wire shaft (18) has first and second wire segments (20 and 30), each including a respective distal twisted portion (24 or 34) adjacent its respective distal end (22 or 32). The first wire segment (20) further includes a generally straight portion (26) extending proximally of its distal twisted portion (24), while the second wire segment (30) further includes a hook (36) extending proximally of its distal twisted portion (34).

29 Claims, 2 Drawing Sheets

LOCALIZER NEEDLE

CROSS-REFERENCE TO RELATED APPLICATIONS

This application claims priority of provisional application Ser. No. 60/224,228, filed Aug. 10, 2000.

TECHNICAL FIELD

This invention relates generally to medical devices, and more particularly, to devices for aiding surgeons in the identification of tissue to be removed from a human or veterinary patient.

BACKGROUND OF THE INVENTION

It has become almost axiomatic that earlier detection of malignancies lead to improved patient survival rates. Improved mammographic techniques, for example, result in the earlier detection of smaller lesions in the breast. Accurate preoperative localization of lesions (that is, the determination of their size and position) serve two important concerns simultaneously: the successful extraction of a suspect lesion, without the removal of unduly large amounts of normal breast tissue. It may of course be desirable to locate cancerous or other tumors, foreign bodies, normal tissue structures or other objects within the body or within an organ of the body. Such locations include the liver, ductal structures, brain, lungs or other portions of a human or veterinary patient.

The localization of lesions which cannot be palpated is of particular concern, precisely since they cannot be palpated by the surgeon during surgery. Lesions may be nonpalpable because they are small in size and therefore difficult to locate (especially in large breasts), or because they are located deep within the tissue mass of the breast. Currently, such lesions are often initially located by radiology or ultrasound, and the lesion marked by a localization needle assembly prior to biopsy or surgery. Such needle assemblies have included a hypodermic needle or cannula which is inserted in the body to an area adjacent to and in contact with the lesion of interest. A marking wire (commonly referred to as a "hookwire" or "hookwire-type" stylet) is then inserted through the needle or cannula into the lesion and anchored in place. The needle or cannula is then removed, leaving the marking wire in place.

One highly useful device which aids in locating nonpalpable lesions within the breast is that devised by Dr. Daniel B. Kopans et al., disclosed, for example, in "A Modified Needle-Hookwire Technique to Simplify Preoperative Localization of Occult Breast Lesions," D. B. Kopans et al., *Radiology*, March, 1980, Vol. 134, page 781; "Versatile Spring Hookwire Breast Lesion Localizer," D. B. Kopans et al., *American Journal of Roentgenology*, March 1982, Vol. 138, pages 586–87; and "Spring Hookwire Breast Lesion Localizer: Use with Rigid-compression Mammographic Systems," *Radiology*, November, 1985, Vol. 157, pages 537–38; all of which are expressly incorporated by reference herein. The hookwire-type stylet or localizer disclosed by Kopans et al. comprises a stainless steel wire having a hairpin hooked-end portion. In the use of a Kopans-type hookwire stylet or localizer, a hypodermic needle is initially placed into the breast to locate a lesion of concern. An attempt is made to aspirate the lesion (via syringe connected to the needle), in case the lesion is a cyst rather than a tumor. If aspiration is unsuccessful, the needle is then positioned adjacent to the lesion, and the location optimally confirmed by using two mammographic positions. When the needle is properly positioned, the Kopans-type hookwire stylet is introduced through the needle. The hook is engaged in the lesion, the proper positioning confirmed and the needle then withdrawn, leaving the stylet in position for surgery.

A preferred embodiment of the Kopans-type stylet 1 is shown in FIG. 1, sold by Cook Incorporated of Bloomington, Ind. The localizer stylet 1 is sold with a thin-wall localization needle (21, 20 19 or 18 gage) 5.0, 9.0 or 15.0 cm in length. (An embodiment having a reinforced portion 2 cm long located 1 cm from the distal tip of the stylet is sold in the same lengths, but only in 21 or 20 gage.) Suitable syringes and other surgical adjuncts are also provided in a kit containing the Kopans-type stylet. A positioning mark 2 is provided on the localizer stylet 1 to provide visual assurance that its spring-hook 3 is contained within the tip of the associated needle during manipulation of the needle. The hook 3 is simply formed by annealing the wire of the stylet 1 and bending it over itself at the annealed location.

The Kopans-type stylet is advantageous over other stylets for several reasons. The stylet is flexible and pliable, and is easily handled during the localizing procedure. Its straightforward construction permits it to be manufactured at a reasonable cost. While very useful for its intended purpose, the Kopans-type stylet is subject to a few drawbacks during use. The stylet is also occasionally subject to movement within the tissue of the patient when the patient moves or when the patient is moved, for example, during or after mammography, or during transport from the radiology lab to the operating room or surgical theater. Such migration may arise because the hook expands into the fatty tissue of the breast.

Other localization needles and devices are known, but each have their own drawbacks. They may be so large and heavy that they are subject to undesirable migration within the patient, either from movement of the patient, or transport of the patient from the location of imaging (typically a radiology lab) to the surgical theater. They may also be so large and heavy that they lack the flexibility and pliability desirable for use. Finally, they may be relatively complex in structure and unduly expensive to manufacture.

It would be highly advantageous to have localizer devices which resisted migration, and perhaps accidental transection by the surgeon during excision, yet which possessed a good degree of flexibility and pliability. It would also be highly advantageous to have such devices which were relatively straightforward in construction and were relatively inexpensive to manufacture.

SUMMARY OF THE INVENTION

The foregoing problems are solved and a technical advance is achieved in an illustrative medical device for localization, that is, establishing the location or position of tissue of surgical interest. According to one aspect of the present invention, there is provided a stylet for use with a medical device, the stylet comprising first and second wire segments each including respective distal ends and respective distal twisted portions adjacent their respective distal ends, the distal twisted portions being twisted about one another, the first wire segment further including an elongated portion extending from the proximal end of its distal twisted portion and the second wire segment extending at least partly laterally from the proximal end of its distal twisted portion and a rounded or curved portion at the distal ends of the first and second wire segments.

According to another aspect of the invention, there is provided a localizer stylet for use with a medical device, the stylet comprising: a shaft comprising first and second wire segments each including respective distal ends and respective distal twisted portions adjacent their respective distal ends, the distal twisted portions being twisted about one another, the first wire segment further including a generally straight portion extending proximally of its distal twisted portion and the second wire segment further including a hook extending proximally of its distal twisted portion, and a rounded portion over the distal ends of the first and second wire segments.

The medical devices of both aspects can most readily be understood as an improvement in Kopans-type or hookwire-type localizer stylet having the wire shaft or longitudinal segment with a distal end, the hook or second segment depending in an at least partly lateral direction from the wire shaft, or elongated wire. The specific improvement of the present invention entails spacing the hook proximally of the distal end of the wire shaft, and providing the wire shaft or segment with a twist at the distal ends. Unexpectedly, this simple expedient significantly improves anchoring of the localizer stylet within the tissue of the patient, thereby reducing the likelihood of undesired migration of the stylet when the patient moves, or is moved or transported.

In the preferred embodiment of the medical device, the localizer stylet comprises first and second wire segments, each wire segment including a distal twisted portion adjacent its respective distal end. The first wire segment extends longitudinally and proximally of its distal twisted portion, while the second wire segment extends from its distal twisted portion in a direction with a lateral component. The localizer stylet of the preferred embodiment of the present invention also includes a rounded portion, such as a bead of solder, at the distal ends of the first and second wire segments. The localizer stylet of the embodiment has several advantages over prior localizer stylets. The embodiment possesses the simplicity of construction
and use enjoyed by prior Kopans-type or hookwire-type localization devices. The potential for breakage at the bend of the prior Kopans-type stylet is avoided, because the present invention does not require any annealing of the wires making up its stylet. Perhaps most significantly, the disclosed stylet is less subject to undesirable changes in position which might otherwise be caused by transport and other movement of the patient between performance of the localization procedure and surgical removal of the tissue of interest.

"Twisted about one another" means that either or both of the portions is twisted about the other. It is likely easier to reliably manufacture embodiments in which both portions are twisted in interlocked, corkscrew shape, but the principle of the present invention is also directed to embodiments in which only one of the portions is twisted about the other. "Twisted about one another" is intended as a shorthand reference to cover both structures. Preferably, the distal twisted portions of the wire segments are twisted twice about each other, that is, at least one of them extends through a curve of about 720°.

Preferably, the hook is straight and is angled away from the generally straight portion of the first wire segment. Also preferably, the first and second wire segments are separate pieces, for example, are composed of stainless steel wire having a circular cross-section. The rounded portion over their distal ends preferably comprises a bead of solder or other suitable medical grade material.

Also preferably, the localizer stylet incorporated in the medical device of the present invention can include a reinforcement near the distal end of the stylet shaft or longitudinal segment. The reinforcement can be a thickened portion of the stylet shaft, but the reinforcement preferably comprises a cannula segment located proximal of the hook, through which the generally elongated portion of the first wire segment extends and is fixed.

As with prior Kopans-type or hookwire-type localizer devices, the medical device of the present invention also preferably comprises a needle assembly dimensioned to receive therethrough the localizer stylet disclosed above, as well as a syringe connectable to the needle assembly. The needle assembly preferably comprises a needle cannula having a proximal end, and a hub disposed about the proximal end of the needle cannula. Advantageously, the proximal end of the needle cannula extends proximally beyond the hub of the needle assembly. The needle cannula is preferably thin-walled, while the hub is preferably lightweight. The stylet shaft conveniently bears on it a marking spaced from its distal end a distance equal to the length of the needle cannula. The marking can be inked or burnished.

In a second aspect, the present invention is directed to a medical device comprising at least a localizer stylet, the stylet comprising: a shaft comprising first and second wire segments each including respective distal ends and respective distal twisted portions adjacent their respective distal ends, the distal twisted portions being twisted twice about one another; the first wire segment further including a generally straight portion extending proximally of its distal twisted portion, and the second wire segment further including a hook extending proximally of its distal twisted portion; a rounded portion over the distal ends of the first and second wire segments; a needle assembly dimensioned to receive the localizer stylet therethrough; and a syringe connectable to the needle assembly; wherein the hook is straight and is angled away from the generally straight portion of the first wire segment; wherein the first and second wire segments are separate pieces and are composed of stainless steel wire having a circular cross-section; wherein the rounded portion comprises solder; and wherein the stylet shaft bears on it a marking spaced from its distal end a distance equal to the length of the needle cannula of the needle assembly.

In another aspect, the present invention is directed to a hookwire-type localizer stylet having a wire shaft with a distal end, and a hook depending from the wire shaft, the improvement wherein the hook is spaced proximally of the distal end of the wire shaft and wherein the wire shaft is twisted between the hook and its distal end.

Other embodiments include a pair of second wire segments extending proximally to respective diverging barbs, and the barb ends can be pointed r beveled to improve anchoring; and a pair of second wire segments twisted about the first with proximal ends diverging to respective ends and also distal ends diverging to respective ends, for anchoring against stress in both directions.

As indicated above, the medical device of the present invention possesses significant advantages over prior devices. It possesses the relative simplicity of construction and use enjoyed by prior Kopans-type or hookwire-type localizers and stylets. At the same time, the potential for breakage at the tip of its stylet is avoided. Moreover, the stylet of the medical device of the present invention is less subject to undesirable changes in position which might otherwise occur during patient transport or movement between the time of the performance of the localization procedure and the time of surgery.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
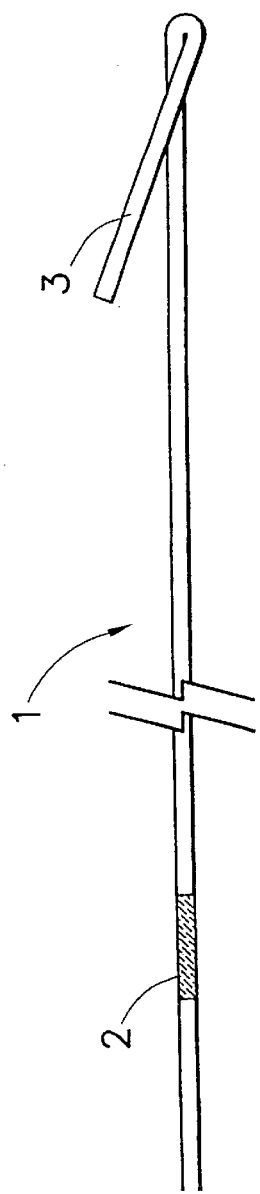
FIG. 1 is a side view of a Kopans-type or hookwire-type localizer stylet of the prior art.
Figure 2:
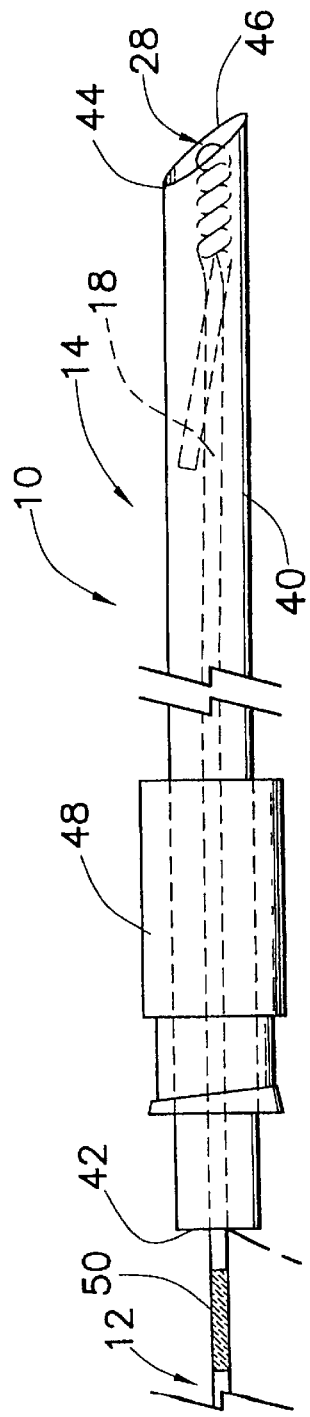
FIG. 2 is a side view of the preferred embodiment of the present invention.
Figure 2:
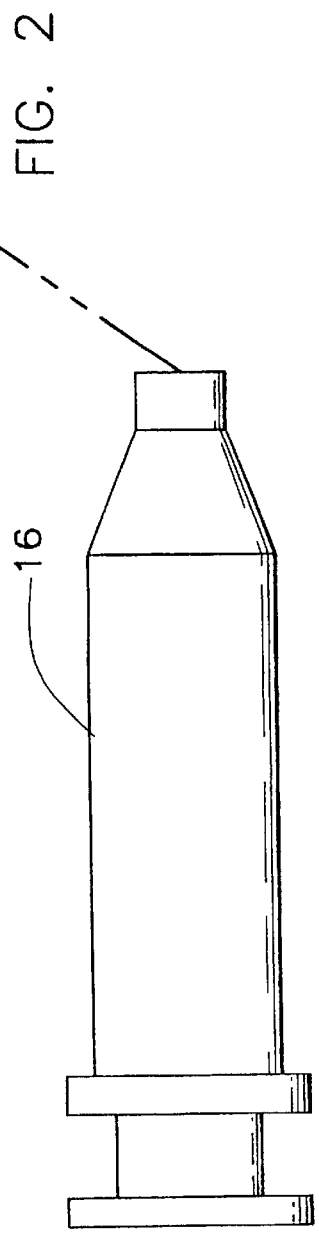
Figure 3:
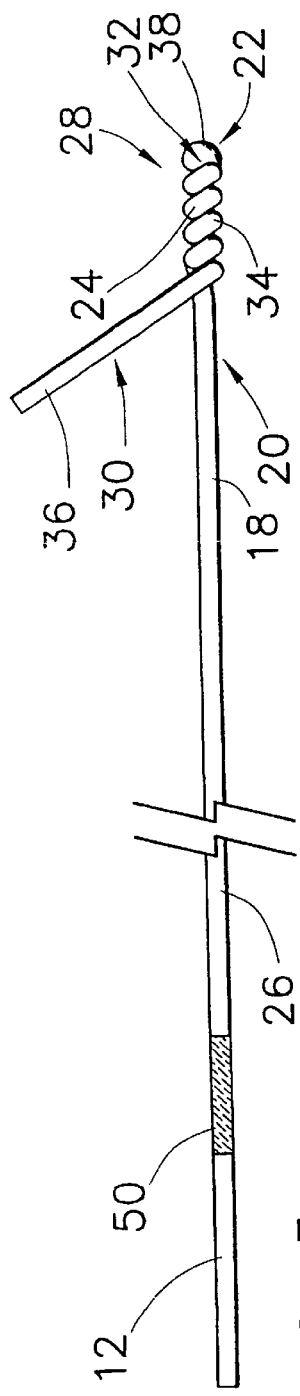
FIG. 3 is a side view of a portion of the preferred embodiment of the present invention.

With reference to FIGS. 2 and 3, a first preferred embodiment of a medical device 10 according to the present invention is thereshown, useful for establishing the location or position of tissue of surgical interest, for example, a nonpalpable lesion in the breast. Considered most simply, the medical device 10 of the present invention comprises at least a localizer stylet 12 of the Kopans-type or hookwire-type (hereinafter, both types referred to as "hookwire-type" stylets) having a wire shaft 18 with a distal end 28, and a hook 36 depending from the wire shaft 18 in a proximal direction. The present invention is the improvement in hookwire-type localizer devices wherein the hook 36 is spaced proximally of the distal end 28 of the wire shaft 18, and wherein the wire shaft 18 is twisted between the hook 36 and the distal end 28 of the wire shaft 18.

More particularly, the medical device 10 of the present invention comprises at least a localizer stylet 12, the stylet 12 in turn first comprising a shaft 18. The shaft 18 comprises first and second wire segments 20 and 30. Each of the first and second wire segments 20 and 30 include a respective distal end 22 or 32, and a respective distal twisted portion 24 or 34 adjacent its respective distal end 22 or 32. The distal twisted portions 24 and 34 are twisted about one another, preferably, for example, twisted twice about each another. "Twisted twice about one another" (or "each" other) means that at least one of the distal twisted portions 24 and 34 extends through a curve of about 720°. Preferably, both of the distal twisted portions 24 and 34 extend through such a curve. The number of times the distal twisted portions 24 and 34 are twisted about one another should be selected as needed to achieve any particularly desired degree of anchoring, in light of the tissue in which it is intended to deploy the localizer stylet 12.

The first wire segment 20 of the stylet shaft 18 further includes a generally straight portion 26 extending proximally of its distal twisted portion 24. The second wire segment 30 of the stylet shaft 18 further includes a hook 36 extending proximally of its distal twisted portion 34. The hook 36 is preferably straight, about 1 cm in length, and is preferably angled about 20° away from the generally straight portion 26 of the first wire segment 20.

While it is contemplated that the first and second wire segments 20 and 30 could be constituted from a single piece of wire (and as explained below, are preferably manufactured from a single piece of wire), it is preferred that the first and second wire segments 20 and 30 are separate pieces of wire. More preferably, the first and second wire segments 20 and 30 are composed of stainless steel or other medical grade wire having a circular cross-section.

The localizer stylet 12 of the medical device 10 of the present invention also comprises a rounded portion 38 over the distal ends 22 and 32 of the first and second wire segments 20 and 30, respectively. The rounded portion 38 may be formed in any convenient manner, for example, as a bead of solder on the distal ends 22 and 32 of the first and second wire segments 20 and 30. The rounded portion 38 can also be formed by welding together the distal ends 22 and 32 of the first and second wire segments 20 and 30.

The medical device 10 of the present invention can simply be the localizer stylet 12. Preferably, however, the medical device 10 of the present invention further comprises a needle assembly 14 dimensioned to receive the localizer stylet 12 therethrough. More preferably, the needle assembly 14 comprises a thin-walled needle cannula 40 having a proximal end 42 and a lightweight hub 48 disposed about the proximal end 42 of the needle cannula 40.

Advantageously, the proximal end 42 of the needle cannula 40 extends proximally somewhat beyond the hub 48 of the needle assembly 14, by perhaps about 0.031 to 0.062 in. (0.79 to 1.57 mm). The stylet shaft 18 bears on it a marking 50, the marking 50 being spaced from the distal end 28 of the stylet shaft 18 a distance equal to the full length of the needle cannula 40. Thus, when the localizer stylet 12 is fully received in the needle cannula 40 but does not extend beyond the distal end 44 of the needle cannula 40, the marking 50 remains just visible outside the proximal end 42 of the needle cannula 40 and is not obscured by the hub 48. The distal end 44 of the needle cannula 40 includes a bevel 46 to facilitate penetration of tissue by the needle cannula 40. The marking 50 on the stylet shaft 18 can be inked, burnished or otherwise applied or formed in any convenient manner.

The medical device 10 of the present invention preferably also comprises an aspiration syringe 16 connectable to the hub 48 of the needle assembly 14 when the localizer stylet 12 is not positioned within the needle cannula 40. The syringe 16 is employed in the same fashion as the syringe in the Kopans et al. articles noted above, for attempting to aspirate and drain a suspicious tissue mass or lesion before localization.

Figure 4:
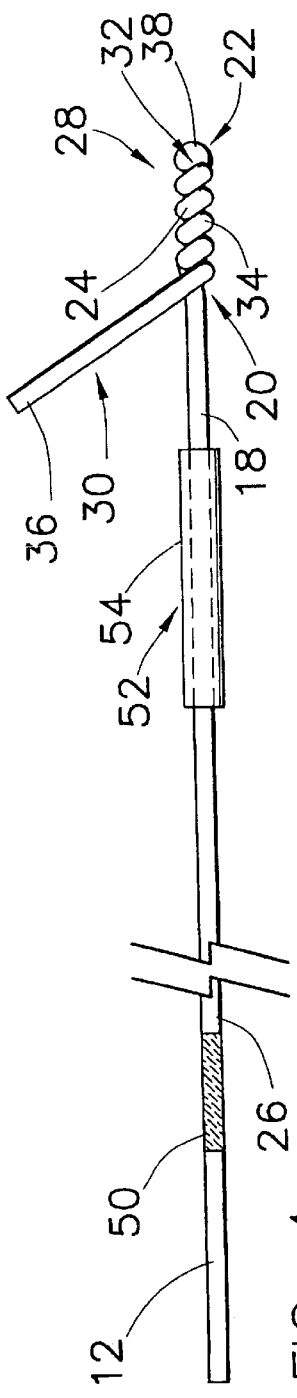
FIG. 4 is a side view of a portion of another preferred embodiment of the present invention.

As shown in FIG. 4, in an alternative preferred embodiment of the present invention, the localizer stylet 12 of the medical device 10 can include a reinforcement 52 near the distal end 28 of the stylet shaft 18, spaced slightly proximal of the hook 36. Typically, the reinforcement 52 will be spaced about 1 cm from the distal end 28 of the stylet shaft 18 and will be about 2 cm in length. Preferably, the reinforcement 52 comprises a cannula segment 54 through which the generally straight portion 26 of the first wire segment 20 extends and in which it is affixed.

Manufacture of the localizer stylet 12 of the medical device 10 is straightforward. The first and second wire segments 20 and 30 of the stylet shaft 18 are preferably cut from the same single piece of wire. More particularly, the ends of the single piece of wire are first arranged into the relative positions and sizes of the hook 36 and the generally straight portion 26, and held in that position by a suitable holder or other device. The bight (that is, the free, slack portion) between the hook 36 and the generally straight portion 26 is then twisted a large number of times (preferably at least several times the number of times the distal twisted portions 24 and 34 are to be twisted about one another) until it is twisted tightly in the area adjacent the hook 36 and generally straight portion 26. The twisted bight is then cut to provide distal twisted portions 24 and 34 of the desired length, and the bead of solder or other rounded portion 38 formed (such as by welding) or applied over the distal ends 22 and 32 of the first and second wire segments 20 and 30.

The dimensions or size of localizer stylet 12, the needle assembly 14 and the syringe 16 of the medical device 10 of the present invention should be selected in view of the particular lesion or other structure to be localized, and in view of the location of that lesion or other structure within the body of the patient. It is contemplated that the needle cannula 40 can range from 21 to 15 GTW gage, while the first and second wire segments 20 and 30 can each range from 0.010 in. (0.25 mm) to 0.016 in. (0.41 mm) in diameter. If present, the reinforcing cannula segment 54 can then range from 25 to 20 GTW gage. The length of the needle cannula 40, measured from the distal surface of the hub 48, can range from 1.5 cm to 25 cm. (The hub 48 is of course selected as appropriate to the needle cannula 40.) The localizer stylet 12 can then range in length from 10 to 50 cm.

Figure 6:
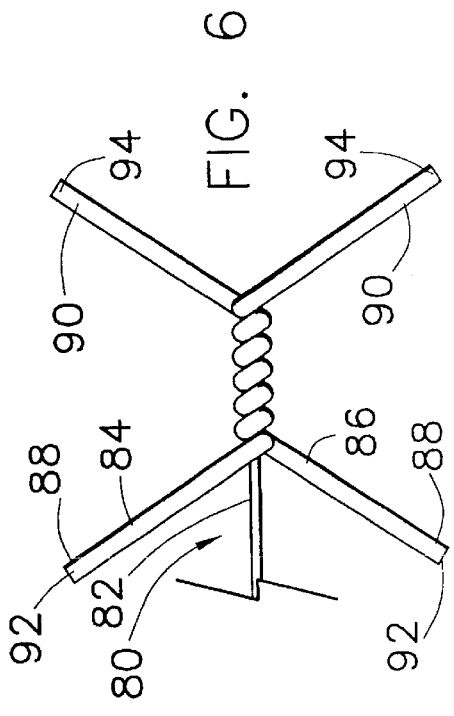
FIGS. 5 and 6 depict alternate embodiments with a pair of barbs and two pairs of barbs, respectively.
Figure 5:
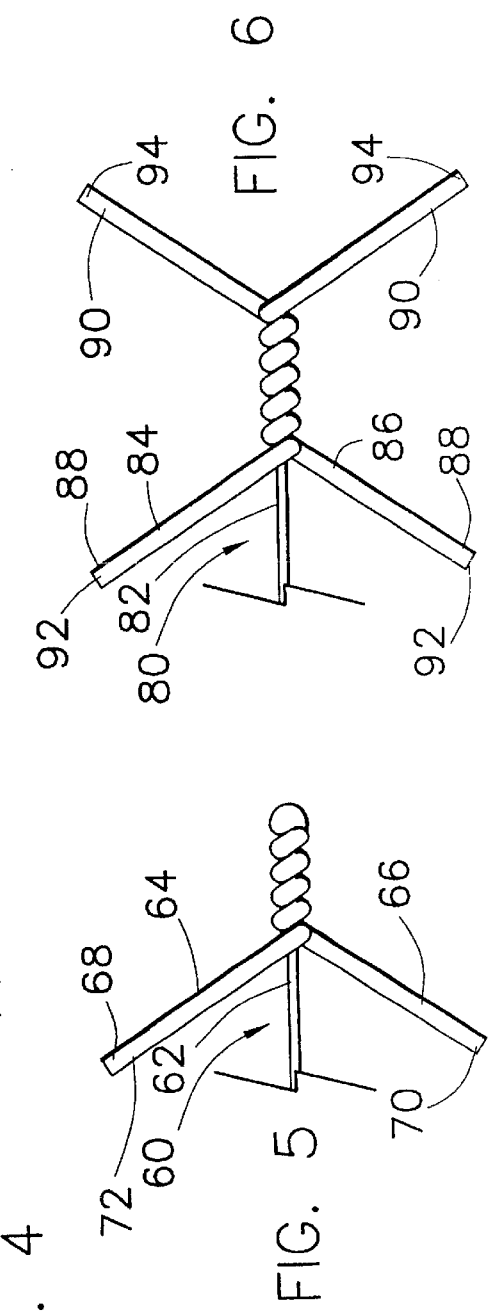

Additional embodiments are shown in FIGS. 5 and 6. Needle 60 of FIG. 5 includes a first wire 62 and a pair of second wires 64,66 that are together twisted with first wire 62, and extend divergingly outwardly and proximally to hooks 68,70. Ends 72 can be pointed or beveled to improve anchoring. Needle 80 of FIG. 6 also includes a first wire 82 and a pair of second wires 84,86 that are together twisted with first wire 82. However, both ends 88,90 of each of the second wires define hooks 92 with the ends 88 diverging extending proximally and ends 90 diverging extending distally to hooks 94. Needle 80 is adapted to provide assured anchoring against stress in either direction once placed.

The medical device 10 of the present invention and its associated localizer stylet 12 can be employed in the same manner as other hookwire-type localizer devices. The various requirements and methods of using such devices are more than adequately disclosed in the Kopans et al. articles mentioned above, and should be well known to those skilled in the surgical arts. Accordingly, such requirements and methods need not and for brevity will not be recited here.

The present invention thus provides a medical device 10 which is particularly useful for establishing the location or position of a nonpalpable lesion or other tissue of surgical interest. The present invention is particularly advantageous in that it possesses the relative simplicity of construction and use enjoyed by prior Kopans-type or hookwire-type localizers and stylets while avoiding the potential for breakage or fracture to which they are subject. Moreover, the stylet of the medical device of the present invention is less subject to undesirable changes in position which might otherwise occur during patient transport or movement between the performance of the localization procedure and the performance of the desired surgery.

The details of the construction or composition of the various elements of the medical device 10 of the present invention not otherwise disclosed are not believed to be critical to the achievement of the advantages of the present invention, so long as the elements possess the strength or mechanical properties needed for them to perform as disclosed. The selection of any such details of construction are believed to be well within the ability of one of even rudimentary skills in this area, in view of the present disclosure. For practical reasons, however, most embodiments of the medical device 10 of the present invention should probably be considered to be single-use devices, rather than being reusable.

INDUSTRIAL APPLICABILITY

The present invention is useful for establishing the location or position of tissue of surgical interest within a human or veterinary patient, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A stylet for use with a medical device (10), the stylet (12) comprising:

first and second wire segments (20 and 30) each including respective distal ends (22 and 32) and respective distal twisted portions (24 and 34) adjacent their respective distal ends (22 and 32), the distal twisted portions (24 and 34) being twisted about one another; the first wire segment (20) further including an elongated portion (26) extending from the proximal end of its distal twisted portion (24), and the second wire segment (30) extending at least partly laterally from the proximal end of its distal twisted portion (34); and a rounded or curved portion (38) at the distal ends (22 and 32) of the first and second wire segments (20 and 30).

2. A stylet according to claim 1, wherein the second wire segment (30) is substantially straight, and when unconstrained is angled away from the first wire segment (20).

3. A stylet according to claim 2, further including a third wire segment that is substantially straight extending from a distal twisted portion that is twisted together with the distal twisted portions of the first and second wire segments, and when unconstrained is angled away from the first wire segment from the opposite side thereof than the second wire segment.

4. A stylet according to claim 3, wherein the second and third wire segments include distal portions that extend substantially straight distally from the distal twisted portions thereof and when unconstrained are angled away from the axis of the first wire segment.

5. A localizer stylet (12) for use with a medical device (10), the stylet (12) comprising:

a shaft (18) comprising first and second wire segments (20 and 30) each including respective distal ends (22 and 32) and respective distal twisted portions (24 and 34) adjacent their respective distal ends (22 and 32), the distal twisted portions (24 and 34) being twisted about one another; the first wire segment (20) further including a generally straight portion (26) extending proximally of its distal twisted portion (24), and the second wire segment (30) further including a hook (36) extending proximally of its distal twisted portion (34); and a rounded portion (38) over the distal ends (22 and 32) of the first and second wire segments (20 and 30).

6. The localizer stylet (12) according to claim 5, wherein the hook (36) is straight and is angled away from the generally straight portion (26) of the first wire segment (20).

7. The localizer stylet according to claim 6, further including a third wire segment that is substantially straight extending from a distal twisted portion that is twisted together with the distal twisted portions of the first and second wire segments, and when unconstrained is angled away from the first wire segment from the opposite side thereof than the second wire segment.

8. The localizer stylet according to claim 7, wherein the second and third wire segments include distal portions that extend substantially straight distally from the distal twisted portions thereof and when unconstrained are angled away from the axis of the first wire segment.

9. The localizer stylet (12) according to claim 5, wherein the first and second wire segments (20 and 30) are separate pieces.

10. The localizer stylet (12) according to claim 5, wherein the first and second wire segments (20 and 30) are composed of wire having a circular cross-section.

11. The localizer stylet (12) according to claim 5, wherein the rounded portion (38) comprises solder.

12. The localizer stylet (12) according to claim 5, wherein the distal twisted portions (24 and 34) of the first and second wire segments (20 and 30) of the shaft (18) are twisted twice about each other.

13. The localizer stylet (12) according to claim 5, further comprising a needle assembly (14) dimensioned to receive the localizer stylet (12) there-through.

14. The localizer stylet (12) according to claim 5, wherein the stylet shaft (18) has a distal end (28), and wherein the localizer stylet (12) includes a reinforcement (52) near the distal end (28) of the stylet shaft (18).

15. The localizer stylet (12) according to claim 14, wherein the reinforcement (52) of the localizer stylet (12) comprises a cannula segment (54) proximal of the hook (36), through which the generally straight portion (26) of the first wire segment (20) extends.

16. The localizer stylet (12) according to claim 5, wherein the first and second wire segments (20 and 30) comprise medical grade stainless steel.

17. A medical device (10) comprising the localizer stylet according to claim 5, and further comprising a needle assembly (14) dimensioned to receive the localizer stylet (12) therethrough when the second wire segment (30) is in a proximally extending position.

18. The medical device according to claim 17, wherein the needle assembly (14) comprises a needle cannula (40) having a proximal end (42), and a hub (48) disposed about the proximal end (42) of the needle cannula (40).

19. The medical device (10) according to claim 18, wherein the hub (48) of the needle assembly (14) is lightweight.

20. The medical device (10) according to claim 19, wherein the proximal end (42) of the needle cannula (40) extends proximally beyond the hub (48) of the needle assembly (14).

21. The medical device (10) according to claim 19, wherein the needle cannula (40) of the needle assembly (14) is thin-walled.

22. The medical device (10) according to claim 18, wherein the stylet shaft (18) has a distal end (28) and bears on it a marking (50) spaced from its distal end (28) a distance equal to the length of the needle cannula (40) of the needle assembly (14).

23. The medical device (10) according to claim 22, wherein the marking (50) is inked.

24. The medical device (10) according to claim 22, wherein the marking (50) is burnished.

25. The medical device (10) according to claim 17, further comprising a syringe (16) connectable to the needle assembly (14).

26. A medical device (10) comprising at least a localizer stylet (12), the stylet (12) comprising:
   a shaft (18) comprising first and second wire segments (20 and 30) each including respective distal ends (22 and 32) and respective distal twisted portions (24 and 34) adjacent their respective distal ends (22 and 32), the distal twisted portions (24 and 34) being twisted twice about one another; the first wire segment (20) further including a generally straight portion (26) extending proximally of its distal twisted portion (24), and the second wire segment (30) further including a hook (36) extending proximally of its distal twisted portion (34);
   a rounded portion (38) over the distal ends (22 and 32) of the first and second wire segments (20 and 30);
   a needle assembly (14) dimensioned to receive the localizer stylet (12) therethrough; and
   a syringe (16) connectable to the needle assembly (14);
   wherein the hook (36) is straight and is angled away from the generally straight portion (26) of the first wire segment (20);
   wherein the first and second wire segments (20 and 30) are separate pieces and are composed of stainless steel wire having a circular cross-section;
   wherein the rounded portion (38) comprises solder; and
   wherein the stylet shaft (18) bears on it a marking (50) spaced from its distal end (28) a distance equal to the length of the needle cannula (40) of the needle assembly (14).

27. In a hookwire-type localizer stylet having a wire shaft (18) with a distal end (28), and a first hook (36) depending from the wire shaft (18), the improvement wherein the first hook (36) is spaced proximally of the distal end (28) of the wire shaft (18) and wherein the wire shaft (18) is twisted between the hook (36) and its distal end (28).

28. The localizer stylet of claim 27, further having a second hook depending from the wire shaft spaced proximally of the distal end of the wire shaft laterally opposite the first hook and diverging therefrom.

29. The localizer stylet of claim 28, further having third and fourth hooks depending from the wire shaft spaced distally of the distal end of the wire shaft and diverging toward opposing lateral sides.

* * * * *